US011883331B2

(12) United States Patent
Rumpke et al.

(10) Patent No.: US 11,883,331 B2
(45) Date of Patent: Jan. 30, 2024

(54) ARC TIME RECORDING SYSTEM FOR AUTO-DARKENING WELDING HELMET

(71) Applicant: Lincoln Global, Inc., Santa Fe Springs, CA (US)

(72) Inventors: Paul H. Rumpke, Cleveland, OH (US); Richard D. Smith, Hudson, OH (US); Bruce J. Chantry, Solon, OH (US)

(73) Assignee: LINCOLN GLOBAL, INC., Santa Fe Springs, CA (US)

( * ) Notice: Subject to any disclaimer, the term of this patent is extended or adjusted under 35 U.S.C. 154(b) by 885 days.

(21) Appl. No.: 16/736,916

(22) Filed: Jan. 8, 2020

(65) Prior Publication Data

US 2020/0397616 A1 Dec. 24, 2020

Related U.S. Application Data

(60) Provisional application No. 62/930,630, filed on Nov. 5, 2019, provisional application No. 62/863,573, filed on Jun. 19, 2019.

(51) Int. Cl.
*B23K 9/09* (2006.01)
*A61F 9/06* (2006.01)
*B23K 9/095* (2006.01)
*G01D 5/12* (2006.01)
*G01J 1/18* (2006.01)

(52) U.S. Cl.
CPC ............ *A61F 9/067* (2013.01); *B23K 9/0956* (2013.01); *G01D 5/12* (2013.01); *G01J 1/18* (2013.01)

(58) Field of Classification Search
CPC ......... A61F 9/067; A61F 9/06; B23K 9/0956; B23K 9/322; B23K 9/095; G01D 5/12; G01J 1/0219; G01J 1/0418; G01J 1/18; G01J 1/26; G01J 2001/0276
See application file for complete search history.

(56) References Cited

U.S. PATENT DOCUMENTS

| 5,248,880 A | 9/1993 | Fergason |
| 7,161,135 B2 | 1/2007 | Fergason |
| 9,566,192 B2 | 2/2017 | Becker et al. |
| 9,867,737 B2 | 1/2018 | Fergason |
| 10,251,786 B2 | 4/2019 | Yang |

(Continued)

FOREIGN PATENT DOCUMENTS

| JP | H0811293 B2 * | 2/1996 | ............. B23K 9/095 |
| KR | 10-1851540 B1 | 4/2018 | |
| KR | 1851540 B1 * | 4/2018 | ............... A61F 9/06 |

OTHER PUBLICATIONS

Espacenet English Translation of Huh KR 101851540 B1 (Year: 2016).*

(Continued)

*Primary Examiner* — Jermele M Hollington
*Assistant Examiner* — Courtney G Mcdonnough
(74) *Attorney, Agent, or Firm* — David J. Muzilla (57) ABSTRACT

A welding helmet can record a welding time based on an arc intensity detected by a sensor mounted on the helmet. A configured level is compared with the arc intensity detected by the sensor to determine a welding duration. Individual welding times from multiple welding instances can be accumulated over a period of time to provide a total welding time for an operator. The total welding time may be stored in the welding helmet.

19 Claims, 5 Drawing Sheets

(56) References Cited

U.S. PATENT DOCUMENTS

| | | | |
|---|---|---|---|
| 2006/0185052 A1* | 8/2006 | Huh | A61F 9/06 |
| | | | 2/8.2 |
| 2009/0094721 A1 | 4/2009 | Becker | |
| 2013/0291271 A1* | 11/2013 | Becker | B23K 9/16 |
| | | | 2/8.2 |
| 2016/0228971 A1* | 8/2016 | Kowaleski | B23K 9/0956 |
| 2016/0267806 A1 | 9/2016 | Hsu et al. | |
| 2018/0290226 A1 | 10/2018 | Huh | |
| 2019/0175411 A1 | 6/2019 | Awiszus et al. | |

OTHER PUBLICATIONS

Ador Welding; "Auto Darkening Welding Helmet;" Originally Accessed on Jun. 21, 2019 ; pp. 1-6.

The Welder; "Welding helmets in view: Five welding helmets, five sets of capabilities," https://www.thefabricator.com/thewelder/article/safety/welding-helmets-in-view; Dated Jan. 15, 2008; pp. 1-5.

Honeywell; "Optrel Welding Protection" Catalogue; Dated May 2012; pp. 1-16.

Miller; "T94 Series Welding Helmets;" https://www.millerwelds.com/safety/helmets/t94-series-welding-helmets-m30140; Originally Accessed on Jun. 21, 2019; pp. 1-8.

Miller; "InfoTrack Products;" https://www.millerwelds.com/technologies/infotrack; Originally Accessed on Jun. 21, 2019; pp. 1-2.

* cited by examiner

ARC TIME RECORDING SYSTEM FOR AUTO-DARKENING WELDING HELMET

INCORPORATION BY REFERENCE

The present application claims priority to Provisional Patent Application 62/863,573, filed Jun. 19, 2019, which is incorporated herein by reference in its entirety. The present application also claims priority to Provisional Patent Application 62/930,630, filed Nov. 5, 2019, which is incorporated herein by reference in its entirety.

TECHNICAL FIELD

In general, the present invention relates to helmets for arc welding and, in particular, to techniques for recording arc time in a welding helmet.

BACKGROUND OF THE INVENTION

Using vision protection, for example using goggles or a welding helmet, is commonly practiced during welding operations by an operator. A welding helmet, for instance, may include a darkened face plate or lens that reduces exposure to light from an arc. The lens may be constantly darkened such that the welding helmet is configured to flip up to allow an operator to see normally and flip down to protect the operator during welding. Alternatively, the lens may include an auto-darkening filter capable of transitioning between a reduced shaded state (e.g. mostly transparent) and a highly shaded state (e.g. darkened) similar to a standard welding helmet lens.

SUMMARY OF THE INVENTION

The following summary presents a simplified summary in order to provide a basic understanding of some aspects of the devices, systems, and/or methods discussed herein. This summary is not an extensive overview of the devices, systems, and/or methods discussed herein. It is not intended to identify critical elements or to delineate the scope of such devices, systems, and/or methods. Its sole purpose is to present some concepts in a simplified form as a prelude to the more detailed description that is presented later.

In accordance with one aspect, a welding helmet is provided that includes an analog optical sensor configured to detect incoming light and output a signal indicative of a light intensity level. The helmet further includes a control circuit configured to receive the signal from the analog optical sensor and record a welding time based on the signal from the analog optical sensor and a configured light level. The welding time corresponds to a duration of time the light intensity level indicated by the analog optical sensor exceeds the configured light level.

These and other aspects of this invention will be evident when viewed in light of the drawings, detailed description and appended claims.

BRIEF DESCRIPTION OF THE DRAWINGS

The invention may take physical form in certain parts and arrangements of parts, at least one embodiment of which will be described in detail in the specification and illustrated in the accompanying drawings, which form a part hereof, and wherein.

DETAILED DESCRIPTION OF THE INVENTION

Embodiments of the invention relate to systems and methods for tracking arc time with a welding helmet. Advanced or sophisticated welding power sources may include features for tracking and maintaining efficiency metrics of operators performing welding operations. Despite the usefulness of such metrics, advanced welding power sources can be too expensive for certain environments. As described herein, a lower cost alternative to features of advanced welding power sources is to outfit a welding helmet with efficiency tracking functionality. In an example, one such metric may track how long an operator spends looking at an active welding arc during a predetermined time period, such as a day or a work shift. According to this example, the welding helmet may include an optical sensor capable of detecting a light intensity incident upon the sensor. A configurable (e.g., user selectable) threshold determines a light intensity above which a counter runs to record welding time. The counter can accumulate individual welding times from individual welding instances. The accumulated welding times may be stored in the welding helmet for later retrieval or reporting. Thus, over a given time frame (e.g. a day), the welding helmet tracks a total amount of time spent welding.

A "welding system" as utilized herein refers to an apparatus or a collection of apparatuses having an implement adapted to perform a welding operation. A welding operation may include, but is not limited to, welding, brazing, soldering, coating, hardfacing, and/or cutting. The implement may include a laser, a waterjet, a flame or an arc generating torch, and/or any other system used in performing the welding operation. In accordance with certain embodiments, the terms "welding" or "weld" (including other formatives of these terms), and in particular arc welding, refers to deposition of molten metal material through operation of an electric arc. Suitable welding processes include, but are not limited to, submerged arc, MIG, MAG, TIG, stick welding, FCAW, etc.

Various embodiments will now be described with reference to the drawings, wherein like reference numerals are used to refer to like elements throughout. In the following description, for purposes of explanation, numerous specific details are set forth in order to provide a thorough understanding of the embodiments. It may be evident, however, that features described herein can be practiced without these specific details. Additionally, other embodiments are possible and the features described herein are capable of being practiced and carried out in ways other than as described. The terminology and phraseology used herein is employed for the purpose of promoting an understanding of the invention and should not be taken as limiting.

Figure 1:
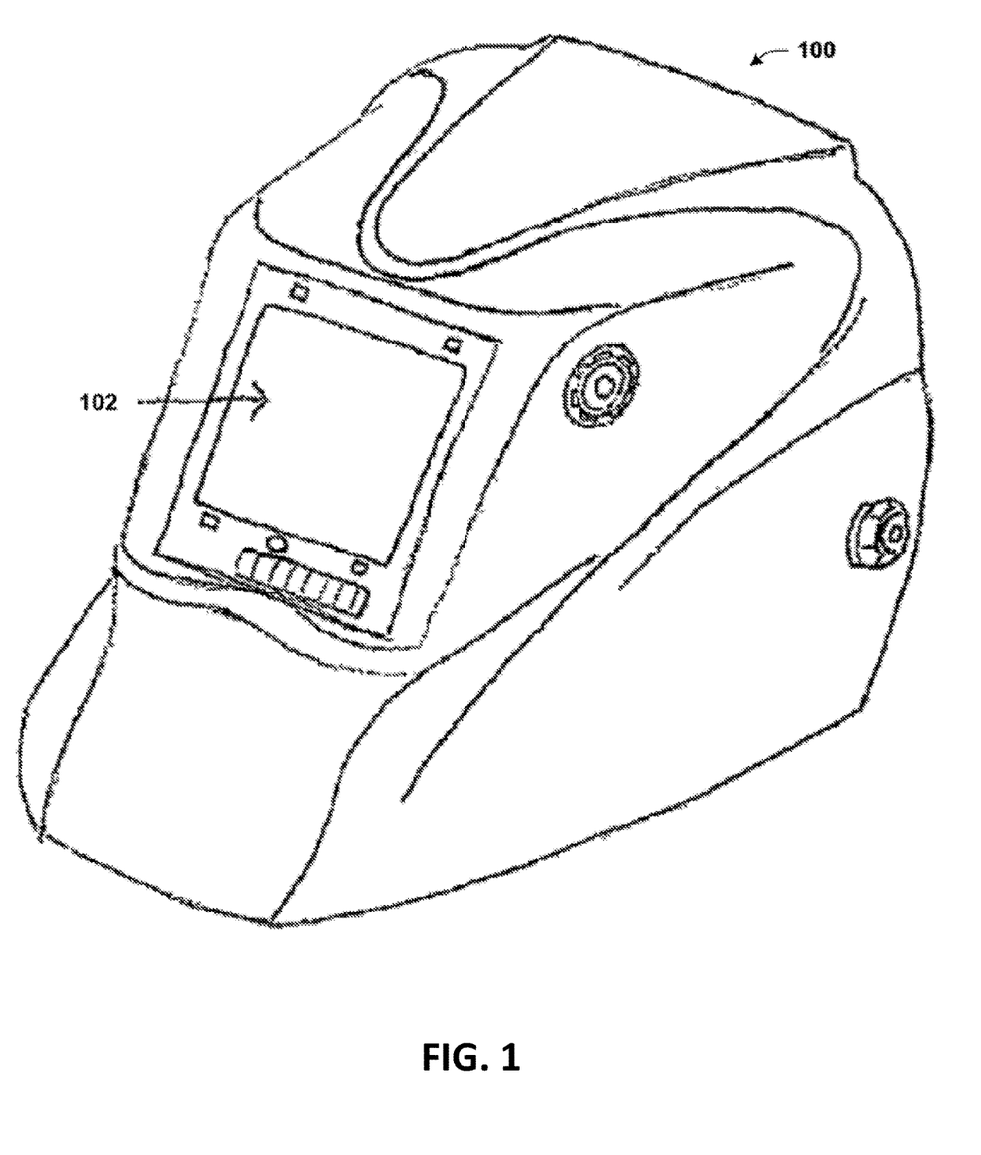
FIG. 1 illustrates an exemplary, non-limiting embodiment of a welding helmet according to one or more aspects.

FIG. 1 illustrates a welding helmet 100 with a faceplate 102 operable to record at least one efficiency metric of an operator (user) performing welding operations. In one embodiment, the faceplate 102 may be an auto-darkening faceplate as described herein. It is to be appreciated that the metric recording described herein may be utilized with a faceplate having a standard lens (e.g. a lens with a constant shade).

Figure 2:
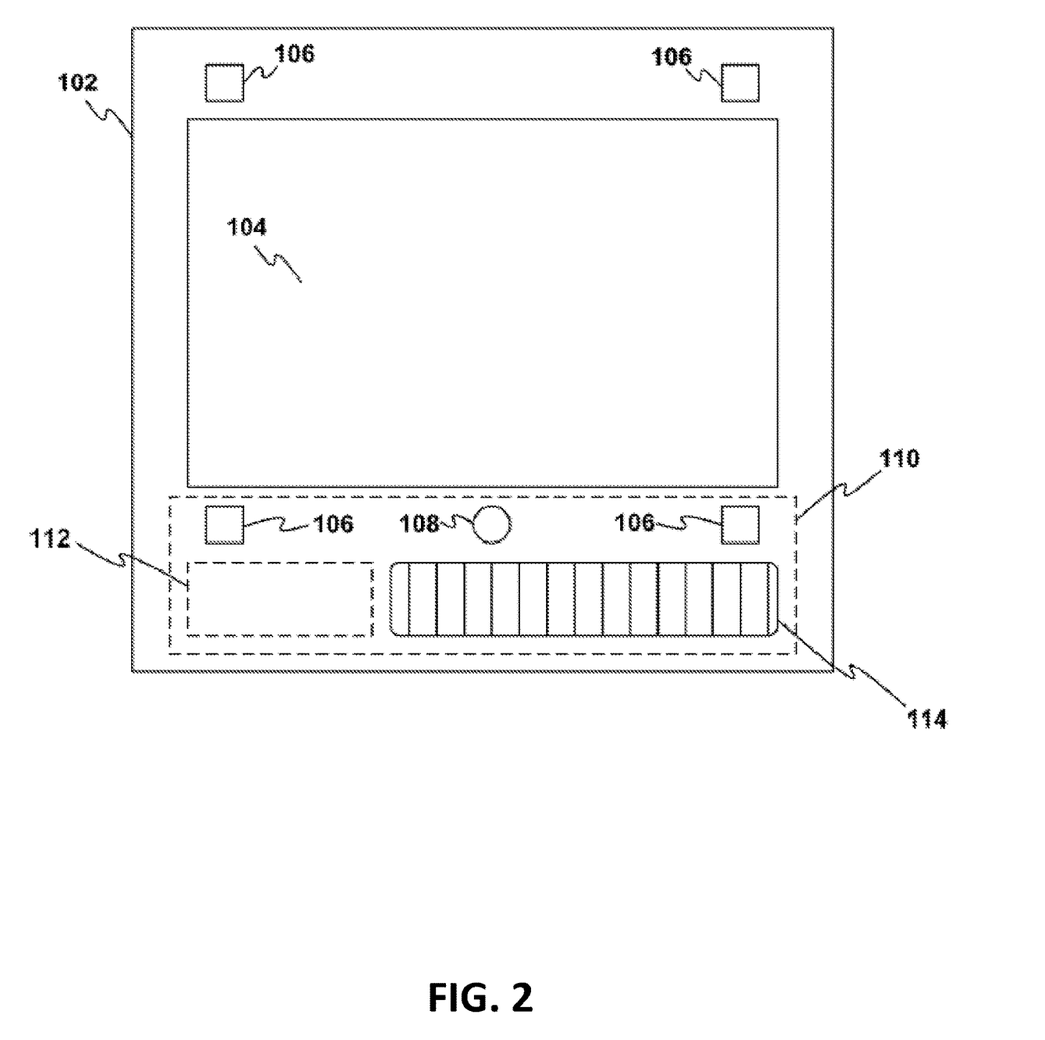
FIG. 2 illustrates an exemplary, non-limiting embodiment of a faceplate for a welding helmet according to various aspects.

Turning to FIG. 2, a detailed view of the faceplate 102 is depicted. The faceplate 102 includes a lens 104 through which the operator views. The lens 104 may be a standard shaded lens or an auto-darkening lens. The auto-darkening lens may be an LCD shade that is switchable between a transparent state and a darkened state through application of an electrical voltage or current. To control the auto-darkening lens 104, the faceplate 102 may include one or more digital optical sensors 106. The digital sensors 106 detect a trigger condition indicative of an arc such as a light intensity greater than a predetermined threshold or a change in light intensity that exceeds a threshold rate. When the trigger condition is detected, the digital sensors 106 emit a signal to a control circuit to transition the lens 104 to a darkened state.

The faceplate 102 may also include an analog optical sensor 108. The analog optical sensor 108 detects light incident on the sensor and outputs a signal indicative of an intensity level. As described in greater detail below, a control circuit utilizes the signal from the analog optical sensor 108 to determine when to start and stop a counter 119 (see FIG. 3) that measures welding time. For example, a configurable intensity level may be set that triggers the counter 119. When the sensed intensity exceeds the configured level, the counter 119 is started. When the intensity subsequently falls below the configured level, the counter 119 is stopped.

The faceplate 102 may also include a user interface 110. The user interface 110 is on a reverse side (operator side) of the faceplate 102. The user interface 110 may include input devices such as a buttons, switches, dials, etc. to enable the operator to manually adjust settings of the helmet 100. The user interface 110 may also include a display to output settings or a measured welding time.

A control circuit 112 is provided to control the counter 119 based on the analog optical sensor, to control the lens 104 based on the digital sensors 106, adjust settings or execute commands input via the user interface 110, and/or output information to the operator via the display. The counter 119 may be a component of the control circuit or may be a standalone component, in accordance with various embodiments. The faceplate 102 may also include a rechargeable solar cell 114 to provide power to the control circuit 112, the user interface 110, the analog optical sensor 108, the digital sensors 106, and/or the lens 104.

Figure 3:
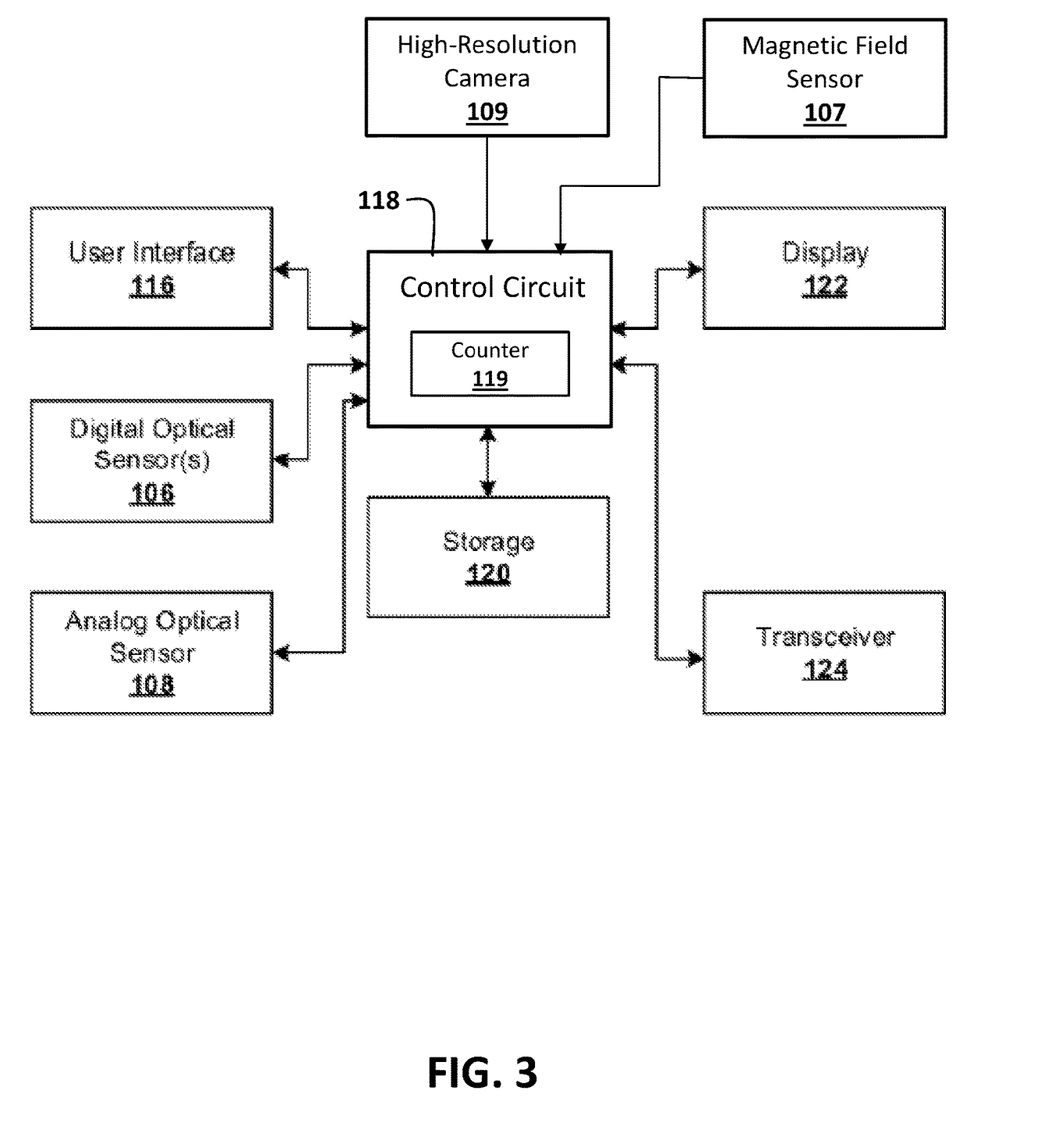
FIG. 3 illustrates a block diagram of components of a welding helmet according to an exemplary, non-limiting embodiment.

Turning to FIG. 3, a block diagram of components of a welding helmet is illustrated. The components shown in FIG. 3 may be included in the helmet 100 and/or the faceplate 102 described above. A control circuit 118 may receive input from the user interface 116, the digital optical sensors 106, and the analog optical sensor 108. The input from the user interface 116 may include, for example, a reset signal to reset stored values (e.g., weld times) or settings, or an adjustment signal to change a configurable threshold. The digital sensors 106 may provide a switching or trigger signal to the control circuit 118 to determine a state of an auto-darkening lens (not shown). The analog sensor 108 outputs an intensity signal to the control circuit 118 that is indicative of a light intensity level received by the sensor 108.

The control circuit 118 may communicate with a storage device 120, which may be a computer-readable storage medium configured to stored measured values such as a recorded welding time or settings such as a configured (e.g., user selectable) light intensity. Further, the control circuit 118 may output information to a display 122 or transmit information via a transceiver 124 to a welding power source or a computing device. Instead of, or in addition to, the analog optical sensor 108, the welding helmet of FIG. 3 may include a magnetic field sensor 107, in accordance with some embodiments, which may output an intensity signal to the control circuit 118 as discussed later herein. Furthermore, instead of, or in addition to, the analog optical sensor 108 and/or the magnetic field sensor 107, the welding helmet of FIG. 3 may include a high-resolution camera 109, in accordance with some embodiments, as discussed later herein.

Figure 4:
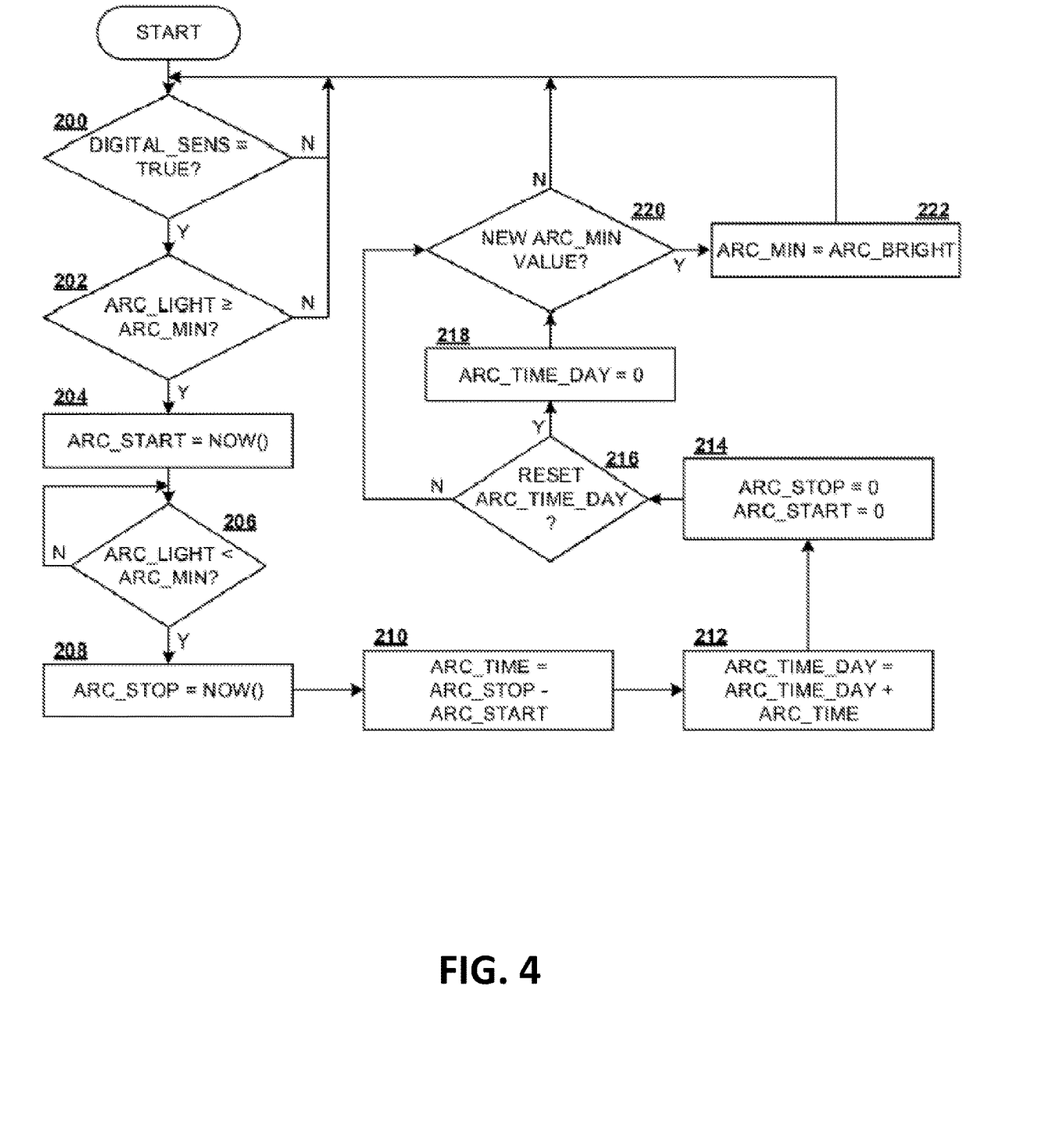
FIG. 4 is a flow diagram of an exemplary, non-limiting embodiment for a control method according to one or more aspects.

Turning to FIG. 4, a flow diagram of a control method is depicted. The control method of FIG. 4 may be performed by the control circuit 118 installed in a welding helmet such as the helmet 100 having the faceplate 102 described above. The method may begin at reference numeral 200 where a determination is made as to whether a trigger signal is acquired from a digital optical sensor. The trigger signal, as described above, would cause a state change in an auto-darkening lens to a shaded state. As shown in FIG. 4, the method may loop until the trigger signal is acquired. When the trigger signal is acquired, a light intensity level acquired from an analog optical sensor is compared to a configured intensity level at 202. If the level reported by the analog optical sensor exceeds the configured level, a start time is captured at 204. If the level does not exceed the configured level, the method returns to the initial loop as shown.

As shown at reference numeral 206, a secondary loop occurs where the control circuit checks the light intensity level reported by the analog optical sensor against the configured level to detect when the reported level falls below the configured level. When the reported intensity level falls below the configured level, a stop time is captured at 208. At reference numeral 210, the captured stop time is subtracted from the captured start time to acquire an arc time or a welding time. This value is indicative of how long the operator was welding during a particular welding instance or arc instance (e.g. a period of time the light intensity was maintained above the configured level). At 212, the calculated arc time is added to a total welding time value that accumulates welding time from all welding instances over a particular period of time (e.g. a day). At 214, the start and stop times are reset (e.g., to zero) to prepare to record a welding time for a next welding instance. At 216, a determination is made as to whether or not to reset the total welding time. For example, a reset signal may be received. If the value should be reset, then the total welding time is reset at reference numeral 218. If the value should not be reset, the method jumps to reference numeral 220 where it is determined if the configured level should be adjusted. For example, an operator may utilize a user interface to adjust the configured level. If the level should be changed, the configured level is set to an input level received via the user interface, for example. After setting the new value, the method returns to the start to repeat for a next welding instance. In accordance with one embodiment, only the welding time for a most recent individual weld is stored (recorded) in memory. Previously recorded weld times for previous individual welds are stored in an accumulated manner as a single accumulated weld time." (e.g., see the flowchart of FIG. 4).

Figure 5:
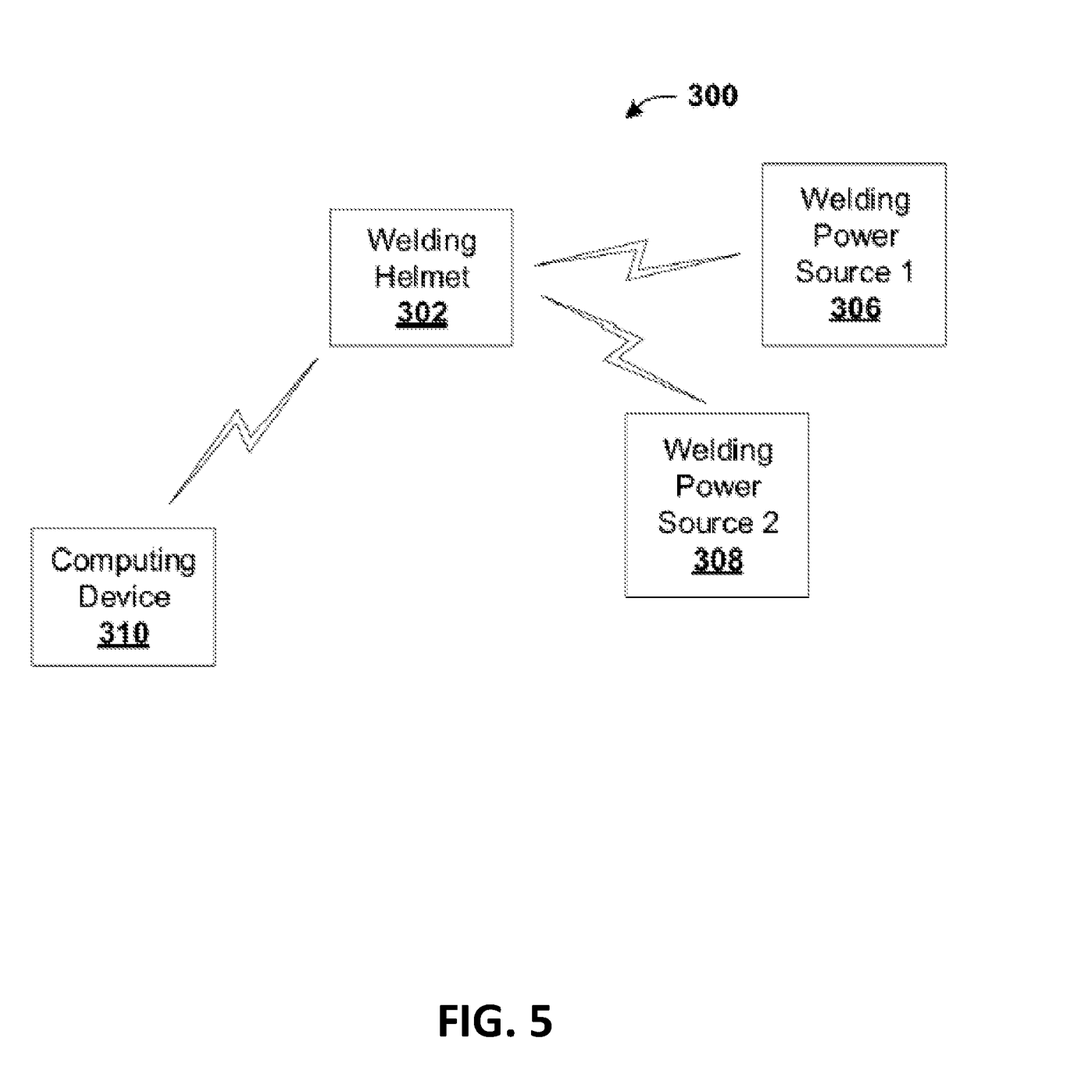
FIG. 5 is a block diagram of an exemplary, non-limiting embodiment of a welding system.

Referring now to FIG. 5, a welding system 300 is illustrated. The welding system 300 may include a welding helmet 302 that may be similar to the helmet 100 described above. The system 300 may also include one or more welding power sources such as power sources 306, 308 and a computing device 310. According to an aspect, the welding helmet 302 may communicate with the welding power sources 306, 308 and/or the computing device 310. For example, the welding helmet 302 may report a welding time to the power sources 306, 308 or to the computing device 310. Moreover, the welding helmet may receive adjustments or reset commands from the power sources 306, 308 or the computing device 310.

In one embodiment, more than one analog optical sensor is provided to determine the minimum light intensity value to start counting arc time. In accordance with one embodiment, a different base unit may be used to record arc time such as seconds per day or hours per day. In one embodiment, another type of sensor such as a high-resolution camera 109 and applicable software to calculate the relative light intensity between the arc and the background environment may be provided. In one embodiment, the arc time data is stored externally rather than inside the auto-darkening filter. In one embodiment, the settings such as the threshold light intensity value and memory data may be adjusted externally rather than with the auto-darkening filter user interface.

In accordance with one embodiment, the trigger to start collecting data is when the threshold light intensity value is higher than the minimum set by the user. This light intensity value is determined by an analog optical sensor and may be higher than the threshold value for the digital optical sensors. For example, the lens filter may darken if a welder places several tack welds to hold two parts together, but the minimum light intensity value to start collecting data may or may not have been exceeded by these welds depending on how high the value was set.

In accordance with one embodiment, instead of (or in addition to) an analog optical sensor, a magnetic field sensor 107 can be used to detect the presence of an arc. The magnetic field sensor 107 detects a magnetic field (or a change in a magnetic field) produced by the arc. As with the optical sensor, a threshold level can be set for a magnetic field level detected by the magnetic sensor to trigger counting of arc duration.

One embodiment includes a welding helmet having an analog optical sensor configured to detect incoming light and to output a signal indicative of a light intensity level of the incoming light. The welding helmet also includes a control circuit configured to receive the signal from the analog optical sensor. The control circuit is also configured to record a welding time based on the signal from the analog optical sensor and a configured light level. The welding time corresponds to a duration of time that the light intensity level indicated by the analog optical sensor exceeds the configured light level. In one embodiment, the configured light level is user selectable. In one embodiment, the control circuit includes a counter configured to determine the welding time. The counter may be hardware based or software based, in accordance with various embodiments. In one embodiment, the welding helmet includes a transceiver configured to transmit (wired or wirelessly) information (e.g., the welding time) to a welding power source or a computing device. In one embodiment, the welding helmet includes an auto-darkening faceplate.

One embodiment includes a welding helmet having an arc detection system configured to detect one or more welding arcs that occur during one or more welding operations. The welding helmet also includes control circuitry configured to lighten or darken a lens assembly of the welding helmet based at least in part on the one or more welding arcs detected by the arc detection system. The control circuitry is also configured to record a duration of an amount of time that the one or more welding arcs are present according to the detection system. The control circuitry is further configured to record only the time of the one or more welding arcs detected by the arc detection system that have an arc intensity value that is greater than a predetermined threshold arc intensity. The welding helmet also includes a storage device configured to store a sum of the duration of the welding arcs over a defined period of time. In one embodiment, the predetermined threshold arc intensity is user selectable. In one embodiment, the arc detection system includes at least one analog optical sensor configured to detect incoming light and output at least one signal indicative of the arc intensity level being an arc light intensity level. In one embodiment, the arc detection system includes at least one magnetic field sensor configured to detect a magnetic field, or a change in a magnetic field, produced by the one or more welding arcs and output at least one signal indicative of the arc intensity level being an arc magnetic field intensity level. In one embodiment, the welding helmet includes a transceiver configured to transmit at least the duration of an amount of time the one or more welding arcs are present according to the arc detection system to a welding power source or a computing device.

One embodiment includes a welding helmet having an arc detection system configured to detect multiple welding arcs that occur during one or more welding operations. The welding helmet also includes control circuitry configured to lighten or darken a lens assembly of the welding helmet based at least in part on the multiple welding arcs detected by the arc detection system and determine a duration of a most recent welding arc of the multiple welding arcs detected by the arc detection system. The control circuitry is also configured to record the duration of the most recent welding arc of the multiple welding arcs detected by the arc detection system that has a respective light intensity value that is greater than a predetermined threshold light intensity. The welding helmet also includes a storage device configured to store a total duration per period of time (e.g., a day, a week, a month, etc.) of at least a portion of the multiple welding arcs detected by the arc detection system. The total duration per period of time of the portion of the multiple welding arcs detected by the arc detection system may include a sum of the duration of welding arcs per period of time of the portion of the multiple welding arcs. In one embodiment, the predetermined threshold arc light intensity is user selectable. In one embodiment, the control circuitry includes a counter configured to determine the duration of the most recent welding arc of the multiple welding arcs detected by the arc detection system. The arc detection system includes at least one of an analog optical sensor, a magnetic field sensor, or a high-resolution camera configured to detect the multiple welding arcs that occur during one or more welding operations.

One embodiment includes a welding helmet having an arc detection system configured to detect one or more welding arcs that occur during one or more welding operations. The welding helmet also includes control circuitry configured to lighten or darken a lens assembly of the welding helmet based at least in part on the one or more welding arcs detected by the arc detection system, and to allow a variable duration of the one or more welding arcs detected to be reset by the arc detection system. The control circuitry is also configured to allow a variable duration of the one or more welding arcs detected to be reset by the arc detection system for welding arcs of the one or more welding arcs that have an arc intensity value that is greater than a predetermined arc intensity. The welding helmet also includes a storage device configured to store the variable duration of the one or more welding arcs detected by the arc detection system that can be reset. A first date provides a reference point relating to an earliest recordable sum of the variable duration of the one or more welding arcs per day. A second date is an earliest date chosen by a user to reset the variable duration of the one or more welding arcs per day. A third date is a latest date chosen by the user to reset the variable duration of the one or more welding arcs per day. In one embodiment, the control circuitry includes a counter configured to determine the variable duration of the one or more welding arcs detected that have an arc intensity value greater than the predetermined arc intensity. In one embodiment, the predetermined arc intensity is user selectable. In one embodiment, the arc detection system includes at least one of an analog optical sensor, a magnetic field sensor, or a high-resolution camera configured to detect the one or more welding arcs that occur during one or more welding operations. In one embodiment, the welding helmet also includes a transceiver configured to transmit at least the variable duration of the one or more welding arcs detected, that have an arc intensity value greater than the predetermined arc intensity, to a welding power source or a computing device.

Any controller, control circuit, or control circuitry in various embodiments of the present invention may include one or more of, for example, a microprocessor, a microcontroller, a programmable logic circuit (PLC), a digital signal processor (DSP), digital logic gates, random access memory (RAM), read only memory (ROM), a digital counter, a user interface (e.g., a touch-screen display), and a network interface. Other elements of a controller, control circuit, or control circuitry are possible as well, in accordance with other embodiments.

The above examples are merely illustrative of several possible embodiments of various aspects of the present invention, wherein equivalent alterations and/or modifications will occur to others skilled in the art upon reading and understanding this specification and the annexed drawings. In particular regard to the various functions performed by the above described components (assemblies, devices, systems, circuits, and the like), the terms (including a reference to a "means") used to describe such components are intended to correspond, unless otherwise indicated, to any component, such as hardware, software, or combinations thereof, which performs the specified function of the described component (e.g., that is functionally equivalent), even though not structurally equivalent to the disclosed structure which performs the function in the illustrated implementations of the invention. In addition although a particular feature of the invention may have been disclosed with respect to only one of several implementations, such feature may be combined with one or more other features of the other implementations as may be desired and advantageous for any given or particular application. Also, to the extent that the terms "including", "includes", "having", "has", "with", or variants thereof are used in the detailed description and/or in the claims, such terms are intended to be inclusive in a manner similar to the term "comprising."

This written description uses examples to disclose embodiments of the invention, including the best mode, and also to enable one of ordinary skill in the art to practice embodiments of the invention, including making and using any devices or systems and performing any incorporated methods. The patentable scope of the invention is defined by the claims, and may include other examples that occur to those skilled in the art. Such other examples are intended to be within the scope of the claims if they have structural elements that are not different from the literal language of the claims, or if they include equivalent structural elements with insubstantial differences from the literal language of the claims.

The best mode for carrying out the invention has been described for purposes of illustrating the best mode known to the applicant at the time. The examples are illustrative only and not meant to limit the invention, as measured by the scope and merit of the claims. The invention has been described with reference to various embodiments. Obviously, modifications and alterations will occur to others upon the reading and understanding of the specification. It is intended to include all such modifications and alterations insofar as they come within the scope of the appended claims or the equivalents thereof.

What is claimed is:

1. A welding helmet, comprising:
    an analog optical sensor configured to detect incoming light and output a signal indicative of a light intensity level; and
    an auto-darkening faceplate; and
    a control circuit configured to:
        receive the signal from the analog optical sensor, and
        record a welding time based on the signal from the analog optical sensor and a configured light level, wherein the welding time corresponds to a duration of time the light intensity level indicated by the analog optical sensor exceeds the configured light level, and wherein the configured light level is higher than a threshold light level where the auto-darkening faceplate transitions between a reduced shaded state and a highly shaded state.

2. The welding helmet of claim 1, wherein the configured light level is user selectable.

3. The welding helmet of claim 1, wherein the control circuit includes a counter configured to determine the welding time.

4. The welding helmet of claim 1, further comprising a transceiver configured to transmit at least the welding time to a welding power source or a computing device.

5. A welding helmet, comprising:
    an arc detection system configured to detect one or more welding arcs that occur during one or more welding operations;
    control circuitry configured to lighten or darken a lens assembly of the welding helmet based at least in part on the one or more welding arcs detected by the arc detection system, and to record a duration of an amount of time the one or more welding arcs are present according to the arc detection system, wherein the control circuitry is configured to record only the time of the one or more welding arcs detected by the arc detection system that have an arc intensity value greater than a predetermined threshold arc intensity; and wherein the predetermined threshold arc intensity is higher than a threshold intensity level where the lens assembly transitions between a lightened state and a darkened state; and
    a storage device configured to store a sum of the duration of the welding arcs over a defined period of time.

6. The welding helmet of claim 5, wherein the predetermined threshold arc intensity is user selectable.

7. The welding helmet of claim 5, wherein the arc detection system includes at least one analog optical sensor configured to detect incoming light and output at least one signal indicative of the arc intensity level being an arc light intensity level.

8. The welding helmet of claim 5, wherein the arc detection system includes at least one magnetic field sensor configured to detect a magnetic field, or a change in a magnetic field, produced by the one or more welding arcs and output at least one signal indicative of the arc intensity level being an arc magnetic field intensity level.

9. The welding helmet of claim 5, further comprising a transceiver configured to transmit at least the duration of an amount of time the one or more welding arcs are present according to the arc detection system to a welding power source or a computing device.

10. A welding helmet, comprising:
an arc detection system configured to detect a plurality of welding arcs that occur during one or more welding operations;
control circuitry configured to lighten or darken a lens assembly of the welding helmet based at least in part on the plurality of welding arcs detected by the arc detection system, to determine a duration of a most recent welding arc of the plurality of welding arcs detected by the arc detection system, and to record the duration of the most recent welding arc of the plurality of welding arcs detected by the arc detection system having a respective arc light intensity value that is greater than a predetermined threshold arc light intensity, wherein the predetermined threshold arc light intensity is higher than a threshold intensity level where the lens assembly transitions between a lightened state and a darkened state; and
a storage device configured to store a total duration per period of time of a portion of the plurality of welding arcs detected by the arc detection system, wherein the total duration per period of time of the portion of the plurality of welding arcs detected by the arc detection system comprises a sum of the duration of welding arcs per period of time of the portion of the plurality of welding arcs.

11. The welding helmet of claim 10, wherein the period of time is one of a day, a week, or a month.

12. The welding helmet of claim 10, wherein the predetermined threshold arc light intensity is user selectable.

13. The welding helmet of claim 10, wherein the control circuitry includes a counter configured to determine the duration of the most recent welding arc of the plurality of welding arcs detected by the arc detection system.

14. The welding helmet of claim 10, wherein the arc detection system includes at least one of an analog optical sensor, a magnetic field sensor, or a high-resolution camera configured to detect the plurality of welding arcs that occur during one or more welding operations.

15. A welding helmet, comprising:
an arc detection system configured to detect one or more welding arcs that occur during one or more welding operations;
control circuitry configured to lighten or darken a lens assembly of the welding helmet based at least in part on the one or more welding arcs detected by the arc detection system, and to allow a variable duration of the one or more welding arcs detected to be reset by the arc detection system for welding arcs of the one or more welding arcs that have an arc intensity value greater than a predetermined arc intensity, wherein the predetermined arc intensity is higher than a threshold intensity level where the lens assembly transitions between a lightened state and a darkened state; and
a storage device configured to store the variable duration of the one or more welding arcs detected by the arc detection system that can be reset, where a first date provides a reference point relating to an earliest recordable sum of the variable duration of the one or more welding arcs per day, a second date is an earliest date chosen by a user to reset the variable duration of the one or more welding arcs per day, and a third date is a latest date chosen by the user to reset the variable duration of the one or more welding arcs per day.

16. The welding helmet of claim 15, wherein the control circuitry includes a counter configured to determine the variable duration of the one or more welding arcs detected that have an arc intensity value greater than the predetermined arc intensity.

17. The welding helmet of claim 15, wherein the predetermined arc intensity is user selectable.

18. The welding helmet of claim 15, wherein the arc detection system includes at least one of an analog optical sensor, a magnetic field sensor, or a high-resolution camera configured to detect the one or more welding arcs that occur during one or more welding operations.

19. The welding helmet of claim 15, further comprising a transceiver configured to transmit at least the variable duration of the one or more welding arcs detected, that have an arc intensity value greater than the predetermined arc intensity, to a welding power source or a computing device.

* * * * *